US006718561B2

(12) United States Patent
Dondero

(10) Patent No.: US 6,718,561 B2
(45) Date of Patent: Apr. 13, 2004

(54) GOGGLE FOR PROTECTING EYES WITH A MOVABLE LENS AND METHODS FOR USING THE GOGGLE

(76) Inventor: John Dondero, P.O. Box 739, Sun Valley, ID (US) 83353

( * ) Notice: Subject to any disclaimer, the term of this patent is extended or adjusted under 35 U.S.C. 154(b) by 9 days.

(21) Appl. No.: 10/011,512

(22) Filed: Nov. 6, 2001

(65) Prior Publication Data

US 2002/0157175 A1 Oct. 31, 2002

Related U.S. Application Data

(60) Provisional application No. 60/288,145, filed on Apr. 30, 2001.

(51) Int. Cl.[7] .................................................. A61F 9/02
(52) U.S. Cl. ....................................................... 2/436
(58) Field of Search ............................ 2/436, 435, 437, 2/441, 443

(56) References Cited

U.S. PATENT DOCUMENTS

| | | | | |
|---|---|---|---|---|
| 4,843,655 A | * | 7/1989 | Hegendorfer ................... | 2/449 |
| 5,542,130 A | * | 8/1996 | Grabos et al. .................. | 2/436 |
| 5,752,280 A | * | 5/1998 | Hill ................................ | 2/453 |
| 6,233,342 B1 | * | 5/2001 | Fernandez ..................... | 381/62 |
| 6,481,025 B2 | * | 11/2002 | Hill ................................ | 2/453 |

OTHER PUBLICATIONS

12 Color photos submitted by Applicant–Killy 950 goggles.*

* cited by examiner

*Primary Examiner*—Katherine Moran
(74) *Attorney, Agent, or Firm*—Graybeal Jackson Haley LLP

(57) ABSTRACT

A goggle comprising a lens, frame, lens-retention mechanism and adjustment mechanism. The lens can be selectively moved relative to the frame to at least two different positions defining substantially different levels of air flow between the lens and frame while maintaining the lens in front of a user's eyes, and retained at each position. One position is defined by substantially all the lens periphery contacting the frame to substantially form a seal. Other positions are defined by substantially all the lens periphery not contacting the frame wherein ambient air flows uninhibited across the inside surface of the lens. The lens-retention mechanism comprises a post and detent, while the adjustment mechanism comprises various mechanisms, for example a rack and pinion, a lever or a rack and pawl that biases the lens to one of the other positions. The adjustment and lens-retention mechanisms may be the same mechanism.

19 Claims, 7 Drawing Sheets

GOGGLE FOR PROTECTING EYES WITH A MOVABLE LENS AND METHODS FOR USING THE GOGGLE

CROSS-REFERENCE TO RELATED APPLICATIONS

This application claims priority from commonly owned U.S. Provisional Patent Application No. 60/288,145 filed Apr. 30, 2001, titled Eye Protection Systems Comprising Of A Moveable Lens And Methods Related Thereto, presently pending, which is hereby incorporated by reference in its entirety.

BACKGROUND

Goggles, masks and other eye-protection systems are very useful to keep dust, wind, gravel, metal shavings and the like out of the eyes. In humid environments and/or during strenuous physical activity a great deal of ventilation between the lens of the goggle or masks and the eyes of the user is highly preferable to prevent or remove condensation from inside the goggles, masks or other systems. In other situations where dust, metal shavings or the like can easily irritate the eyes, a substantially complete seal and/or a partial or filtered seal between the lens and the eyes of a user is desirable.

Unfortunately, in order to vary the amount of ventilation between the lens and eyes of a user, the user typically needs to remove the particular goggle, mask or eye-protection system and put on a different pair. This is expensive because the user needs several different goggles, masks, lenses, etc., and inconvenient because the user must stop whatever they are doing (for example, skiing, snowboarding, motorcycle racing, performing a rescue, etc.) to change the goggle, mask and/or lens. Alternatively, a user can pivot the lens up away-from his eyes, if he/she wears glasses with a pivotable lens commonly known in the art. But, pivoting the lens of these types of glasses results in the lens being located above the eyes in a position where the lens can no longer provide substantial protection to the eyes. Thus, there has gone unmet a need for a goggle, mask and/or lens that is capable of providing a plurality of different ventilation states while maintaining substantial eye protection in each ventilation state.

The present invention provides goggles that comprise a lens which can be set at a plurality of different positions relative to the frame of the goggle so that a plurality of different ventilation states are possible while the lens is maintained in front of at least one eye of a user. The present invention additionally provides other advantages.

SUMMARY

The present invention provides goggles and methods comprising a lens that is selectively moved relative to a frame to increase and/or decrease ventilation of the goggle. Typically, the lens can be moved with or without gloves on the user's hands, and the lens can be permanently or removably attached to the frame. Such goggless and methods are desirable, for example during strenuous activities including sports, technical rescues or military operations, because they make it easy to remove moist air from the enclosed environment between the user's eyes and the lens, yet can substantially prevent dust and debris or the like from injuring the user's eyes. In addition, because extending the lens away from the frame increases ventilation, the frame's profile can be reduced compared to goggles that provide large interior spaces to reduce the effects of inadequate ventilation. With a smaller profile, the goggle can be used in windy environments and also can increase the user's peripheral vision.

Thus, in one aspect, the invention provides a goggle comprising a lens having a lens periphery, a frame having a lens contacting surface and sized to maintain the lens in front of at least one eye of a user. The goggle also comprises a lens-retention mechanism between the lens and the frame that retains the lens in a first position that maintains the lens in front of at least one eye of the user and permits a first level of air flow between the lens and the frame, and in a second position that maintains the lens in front of at least one eye of the user and permits a second, substantially greater level of air flow between the lens and the frame. Furthermore, the goggle comprises an adjustment mechanism between the lens and the frame that moves the lens relative to the frame among the positions. The second position can be defined such that substantially all of the lens periphery is located varying distances away from the lens contacting surface, or the second position can be defined such that a portion of the lens periphery contacts the lens contacting surface. For example the lens can pivot among the positions. The second position can also be defined such that substantially all of the lens periphery is located a first, substantially constant distance away from the lens contacting surface. The goggle can further include more than two lens positions. For example, the eye-protection mechanism can include a third position that maintains the lens in front of at least one eye of the user and permits a third level of air flow between the lens and the frame that is substantially greater than the second level of air flow.

Embodiments of the goggle include various embodiments of the adjustment and lens-retention mechanisms. In some embodiments the lens-retention mechanism and the adjustment mechanism can be the same mechanism. In other embodiments the goggle can comprise two adjustment mechanisms, one on either side of the lens and frame.

In some embodiments, the lens-retention mechanism comprises a post and at least first and second detents sized to receive the post. The detents are located such that when the lens is in the first position the first detent retains the post. In yet other embodiments, the adjustment mechanism comprises a rack and pinion operably connected to the lens and frame to move the lens among the lens positions. In still other embodiments, the adjustment mechanism comprises a lever operably connected to the lens and frame to move the lens among the lens positions. In yet other embodiments, the adjustment mechanism comprises a swing arm operably connected to the lens and frame to move the lens among lens positions.

In still other embodiments, the adjustment mechanism comprises a lens bias spring that biases the lens away from the first position, and the lens-retention mechanism comprises a pawl having a hook and a toothed rack comprising at least first and second teeth. The teeth are located to receive the hook such that when the lens is retained in the first position the pawl is in a restraining position wherein the hook contacts the first tooth and restrains the lens bias spring from moving the lens away from the first position.

Embodiments of the goggle also include various embodiments of the lens to protect a users eyes in various environments. In some embodiments the lens can be removably attached to the frame or can comprises a ballistic grade lens. In these and other embodiments the lens can include a polarized and/or tinted lens. In addition, these and other embodiments of the lens can selectively attenuate infrared light, ultraviolet light, or a narrow range of light wavelengths corresponding to light wavelengths emitted by a laser or a welding torch.

Embodiments of the goggle also include embodiments of the frame that comprise a goggle or glasses. In some of the goggle embodiments the frame also comprises a face-contoured perimeter that forms a substantially air-tight seal with a user's face when the goggle is worn by a user. In addition, some of the goggle embodiments further comprise a goggle-retention member comprising an elastic strap having a length that can be adjustable, a first end connected to a left side of the frame and a second end connected to a right side of the frame.

Embodiments of the goggle also include embodiments of the frame that comprise one or more frame vents to allow inhibited or uninhibited ventilation of the goggle when the lens is at one or more of the lens positions. In some embodiments, the vents can be covered with a filter element.

Embodiments of the goggle also include embodiments of the lens wherein the lens periphery comprises a lens frame. In some of these embodiments, the lens frame comprises at least one lens vent that may or may not be covered with a filter element. Furthermore, in some of these embodiments the frame of the goggle also comprise at least one frame vent that may or may not be covered with a filter element, wherein the lens vent and the frame vent substantially align to form a passage when the lens and frame are in one of the lens positions.

In another aspect, the invention provides a method for retaining and moving a lens relative to a frame in a goggle that comprises placing the lens of a goggle in a first position that maintains the lens in front of at least one eye of the user and permits a first level of air flow between the lens and the frame, retaining the lens in the first position, moving the lens to a second position that maintains the lens in front of at least one eye of the user and permits a second level of air flow between the lens and the frame that is substantially greater than the first level of air flow, and retaining the lens in the second position. In some executions of the method, the method further comprises moving the lens to a third position that maintains the lens in front of at least one eye of the user and permits a third level of air flow between the lens and the frame wherein the third level of air flow is greater than the second level of air flow, and retaining the lens at the third position. In these and other executions of the method, placing and moving the lens can be performed while a user of the goggle is strenuously physically active. In addition, in these and other executions of the method, moving the lens can comprise a) pivoting the lens relative to the frame, b) turning a pinion operably connected to the lens and the frame, c) moving a lever operably connected to the lens and the frame, d) moving a swing arm operably connected to the lens and frame, e) pushing a button operably connected to the lens and the frame to move the lens away from the first position, and pushing the lens to move the lens toward the first position, f) pushing or pulling the lens with at least one of the user's hands.

These and other aspects, features and embodiments are set forth within this application, including the following Detailed Description and attached drawings. The present invention comprises a variety of aspects, features and embodiments; such multiple aspects, features and embodiments can be combined and permuted in any desired manner. In addition, references are set forth herein, including in the Cross-Reference To Related Applications, that discuss certain apparatus, methods or other information; all such references are incorporated herein by reference in their entirety and for all their teachings and disclosures, regardless of where the references may appear in this application.

DETAILED DESCRIPTION

Figure 1:
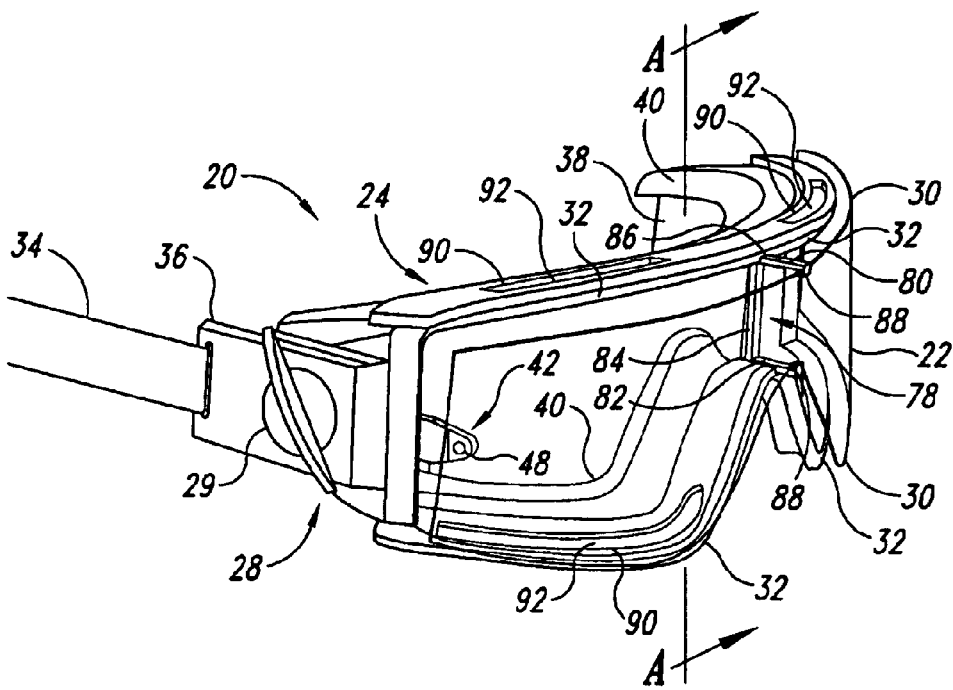
FIG. 1 is a perspective view of a goggle according to one embodiment of the invention.

The present invention provides goggles and methods comprising a lens that is selectively moved between at least two different positions relative to a frame to increase and/or decrease ventilation of the goggle. A first position defines or permits a first level of air flow between the lens and the frame while a second position defines or permits a second, substantially greater, level of air flow between the lens and the frame. The goggles and methods can further provide a third or more positions providing different levels of air flow, if desired. The goggles and methods can maintain the lens in front of the eyes of the user in each of the various positions. To retain the lens in the first and other positions, the goggles comprise a lens-retention mechanism, and to move the lens among the different positions, the goggles comprise an adjustment mechanism. The lens-retention mechanism and the adjustment mechanism can be different mechanisms or they can be a single mechanism; if such mechanisms are different mechanisms, they can be attached to each other or separated from each other. The goggles can comprise one, two or more lens-retention and/or adjustment mechanisms. In some embodiments of the goggle, the lens-retention or adjustment mechanism can, for example, comprise a post and a set of detents, a rack and pawl, a rack and pinion, a button that activates or releases a biasing spring or other device that moves the lens from one position to another, or a lever that moves the lens between positions.

Such goggles and methods are desirable because they maintain the lens in front of at least one eye of the user while permitting different levels of air flow between the lens and the frame, which can permit a user to choose how much air reaches his or her eyes, and can permit the user to adequately vent the goggles, both during periods of strenuous physical activity and during periods of rest—even though the user may be perspiring during such rest periods or moving from a cold area to a warm area that normally would fog the lens. In other words, the goggles and methods are desirable during strenuous physical activities that can include sports, firefighting, performing rescues or performing military operations, and are desirable in industrial labor environments such as metal or wood working shops or in other physically demanding environments, because they facilitate the removal of moist air from the enclosed environment between the user's eyes and the goggle's lens and yet protect the user's eyes from wind, dust, debris or the like. In addition, because extending the lens away from the frame increases ventilation, the frame's profile can be reduced compared to goggles that provide large interior spaces to reduce the effects of inadequate ventilation. With a smaller profile, the goggle can be advantageously used in windy environments and also can increase the user's peripheral vision. The lens can be a single piece lens that covers both eyes, two lenses, one for each eye, or otherwise as desired. The lens can also be bilaterally curved such as spherical or toroidal, or any other desired shape such as conical or cylindrical.

The scope of the present invention includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

All terms used herein, including those specifically described below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

Figure 2:
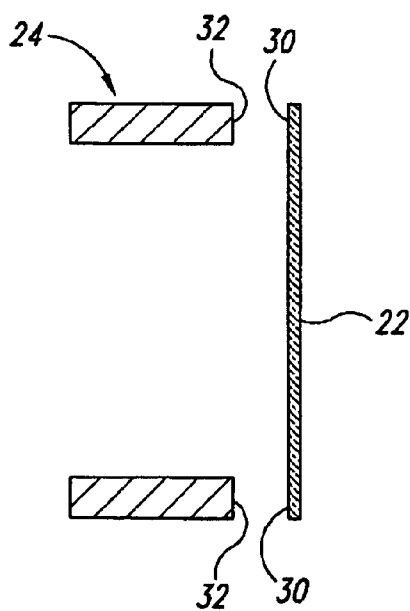
FIG. 2 is a cross-sectional view along line A—A of the goggle in FIG. 1 illustrating the lens extended away from the frame to increase ventilation of the goggle.
Figure 3A:
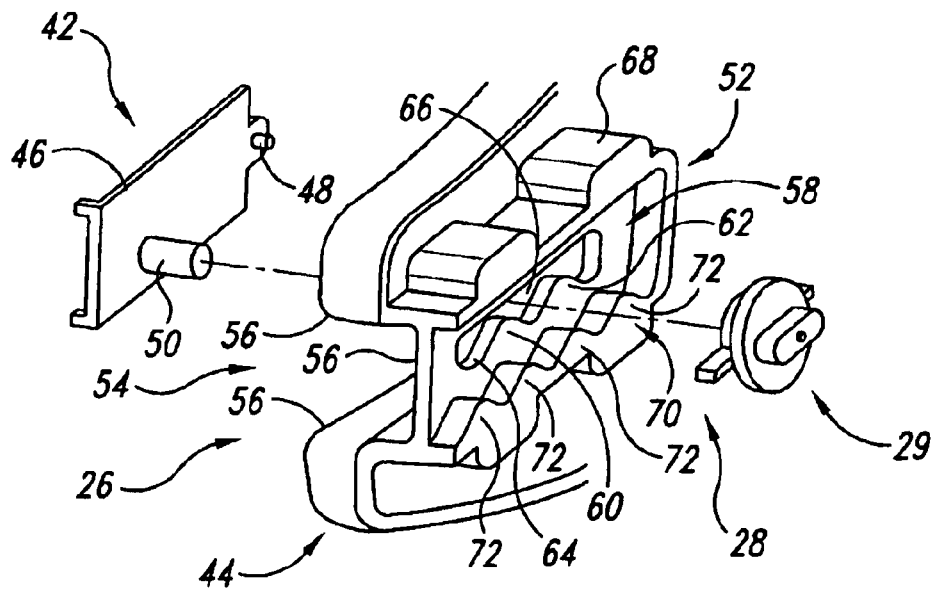
FIG. 3A is an exploded perspective view of the lens-retention and adjustment mechanism shown in FIG. 1.
Figure 3B:
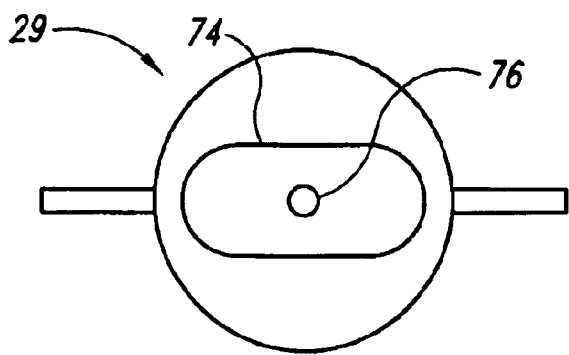
FIG. 3B is a plan view of the pinion shown in FIGS. 1 and 3A.

Turning to the figures, FIGS. 1–3B illustrate a goggle 20 according to one embodiment of the invention. FIG. 1 is a perspective view of the goggle 20, and FIG. 2 is a cross-sectional view of the goggle 20 in FIG. 1 taken at line A—A. The figures illustrate a lens 22 retained in a position relative to a frame 24 that permits open air flow between the lens 22 and frame 24. FIG. 3A is an exploded view of the adjustment mechanism 28 incorporated in the goggle 20 of FIG. 1, which mechanism is connected to both lens 22 and frame 24 and also functions as a lens-retention mechanism (i.e., in this embodiment, the adjustment mechanism 28 and the lens-retention mechanism are the same mechanism). FIG. 3B is a plan view of a pinion 29 incorporated by the lens-retention/adjustment mechanism 28 in FIGS. 1 and 3A.

Referring to FIGS. 1 and 2, the goggle 20 allows a user to quickly, easily and adjustably vent the goggle's enclosed environment. The goggle 20 comprises a lens 22 for protecting the eyes of a user from the ambient environment while allowing the user to see the ambient environment, a frame 24 for maintaining the lens 22 in front of the user's eyes, two adjustment mechanisms 28 (only one shown) between lens 22 and frame 24 that move and also retain the lens 22 relative to the frame 24 in at least a first and second position. In some embodiments, adjustment mechanism 28 can further move lens 22 between at least a third, or more, positions relative to the frame. Lens 22 comprises a lens periphery 30 that contacts lens contacting surface 32 of frame 24. Lens periphery 30 indicates the area of the lens that contacts the frame; typically such area is the outermost reaches of the lens, but other areas of the lens can be used if desired.

The first position (not shown in FIG. 1 or 2) can be defined by the lens 22 being located in front of at least one eye of a user, when the user wears the goggle 20, and substantially all of the lens periphery 30 of the lens 22 contacting the lens contacting surface 32 of the frame 24 to form a substantially air tight seal. Consequently, the first level of air flow can be substantially zero. The first position can alternatively be defined to permit some air passage, for example between vents or discontinuities between lens periphery 30 and lens contacting surface 32 or via (i.e., by use of) vents in the lens 22 or frame 24 or elsewhere as desired, or such air passage can be implemented otherwise as desired. Thus, in some embodiments, only a portion of the lens periphery 30 may contact a portion of the lens contacting surface 32 to permit a substantially nonzero first level of air flow between lens 22 and frame 24 when the lens is in the first position.

Figure 4:
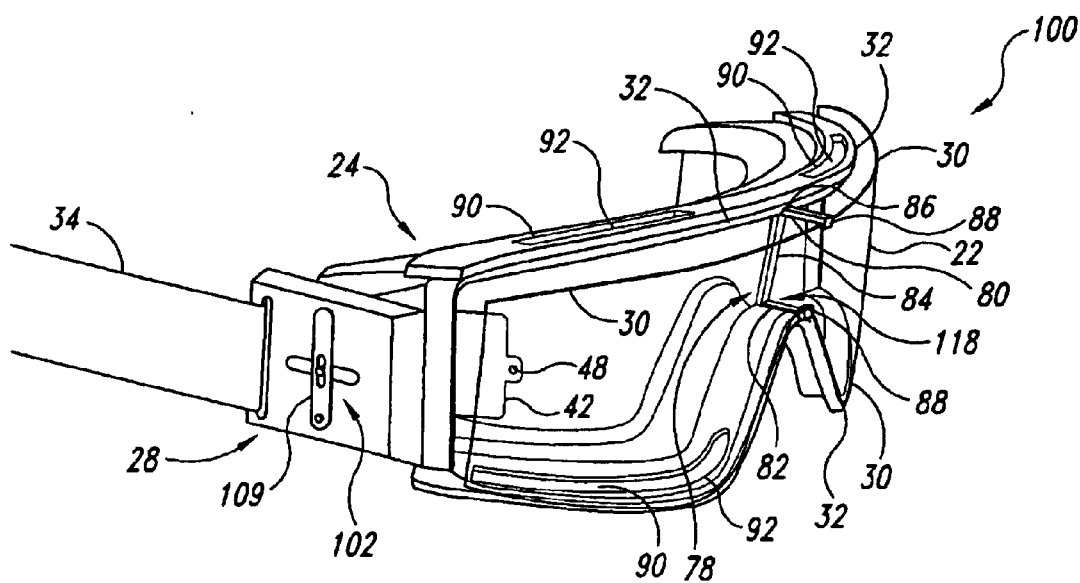
FIG. 4 is a perspective view of a goggle according to another embodiment of the invention.

In the second position, as shown in FIG. 1, lens 22 and frame 24 are moved away from each other relative to their respective locations in the first position, such that the lens 22 is maintained in front of at least one eye of a user, when the user wears the goggle 20, and a substantially greater level of air flow occurs, which means that a significant difference in ventilation between lens 22 and frame 24 is permitted. In some embodiments, the second position can be defined by substantially all of the periphery 30 not contacting the lens contacting surface 32 such that the air tight seal, if the first position defines such, is broken and significant amounts of air can pass between the lens 22 and the frame 24. In the second position substantially all of the lens periphery 30 can be the same distance, or a first distance, away from the lens contacting surface 32. The lens periphery 30 can also be varying distances away from the lens contacting surface 32, for example, discretely varying distances, continuously varying distances, or both, as desired. The varying distances of the second position can substantially all be non-zero distances, or for example as depicted in FIG. 4, a portion of the periphery 30 or other part of the lens may continue to contact the lens contacting surface 32 or other portion of the frame regardless of the position, e.g., the lens may pivot about a portion of the lens contacting surface 32 or two or more sections of the lens 22 may pivot about a common axis or separate axes.

In the third position, the lens 22 is maintained in front of at least one eye of a user, when the user wears the goggle 20, and a third level of air flow is permitted between the lens 22 and the frame 24 that is substantially greater than the air flow permitted in the second position. The third position can be defined by substantially all of the periphery 30 located a substantially constant second distance, which is greater than the first distance, away from the lens contacting surface 32, or the distances between the lens and frame can vary. Although three different lens positions are discussed, more or less positions may be included in the goggle 20. Furthermore, the different lens positions can be discrete or continuous, or otherwise as desired. By retaining the lens 22 in these various positions relative to the frame, the goggle can quickly and easily vent the enclosed environment and thus can hinder the formation of condensation on the inside surface of the lens or facilitate removal of such condensation.

Referring to FIG. 1, when the goggle 20 is worn, the goggle-retention member 34 holds the frame 24 onto the user's face by pulling on the right side 36 and left side 38 of the frame 24. This typically causes the face-contoured perimeter 40 of the frame 24 to forcibly contact the user's face around the eyes and create a substantially air-tight seal between the frame 24 and the user's face. With the lens 22 retained in the first position, the goggle 20 can create an enclosed environment in front of a user's eyes (not shown) such that the frame 24 and the lens 22 can substantially inhibit the ambient air, or other medium outside the enclosed environment, from entering the enclosed environment, and thus can protect the user's eyes. However, during strenuous physical activity or temperature changes, perspiration of a user around his/her eyes or other influences can cause condensation to form on the inside surface of the lens 22. To remove this condensation or reduce the possibility of it forming, the user can extend the lens 22 to the second or third position by operating the adjustment mechanism 28. Once extended, the lens 22 is retained in the second/third position and ambient air can flow uninhibited between the lens 22 and the frame 24. Then, after the moist air is removed from the enclosed environment, the user can simply operate the adjustment mechanism 28 to retract the lens 22 back to the frame 24.

Referring to FIGS. 3A and 3B, in this and certain other embodiments, the adjustment mechanism 28 comprises a lens portion 42 and a frame portion 44. The lens portion 42 comprises a body 46, a lens post 48 and a retention post 50. Retention post 50 is attached to the body 46 and transmits the motion of the pinion 29 to the body 46. Retention post 50 can be made of any resilient material and is appropriately sized to withstand, typically without substantially bending, the force imposed on it. The body 46 can be made of any resilient material that is sufficiently stiff to transmit the force conveyed by retention post 50 to the lens post 48, typically without substantial buckling. The lens post 48 is attached to the lens 22 and transmits the movement of the lens portion 42 to the lens 22. Lens post 48 is attached to the body 46 and can be made of a material sufficiently resilient and stiff to withstand, typically without substantially bending, the force conveyed by the body 46 to the lens 22. As shown in FIG. 3A, the lens and retention posts 48 and 50 are integral to the body 46, but may be attached, releasably or permanently, to the body 46 by other methods such as an adhesive, screw or otherwise as desired.

The frame portion 44 comprises a receiver 52 and a channel 54 formed by walls 56. The size of the channel 54 permits the body 46 to slide within it and typically restrains the body 46 from substantial movement across its length or from substantial rotation. To retain the retention post 50, the receiver 52 comprises a slot 58 sized to receive the retention post 50. Appropriately sized and spaced along the slot 58, a first detent 60 and a second detent 62 define three locations 64, 66 and 68 where the detents 60 and 62 confine the retention post 50 from freely moving among the locations 64–68. These locations 64, 66 and 68 respectively correspond to the first, second and third positions of the lens 22 discussed herein. Although three locations are shown and discussed corresponding to three lens positions, more locations corresponding to more lens positions are possible. Consequently, the slot 58 can have any number of detents to correspond with the number of lens positions.

Still referring to FIGS. 3A and 3B, in this and certain other embodiments, the adjustment mechanism 28 includes a rack and pinion, and more specifically, comprises a pinion 29 that is attached to the lens portion 42 via the retention post 50 (but can be attached to the lens portion 42 via some other component, or directly attached to portion 42) and rotatable relative to the lens and frame portions 42 and 44. The receiver 52 also comprises a rack 70 having four teeth 72 that sequentially contact the boss 74 of the pinion 29. As the pinion 29 rolls over the teeth 72, the boss 74 contacts and pushes against a tooth 72 which causes the center 76 of the pinion 29—where the pinion 29 typically attaches to the retention post 50—to revolve about the point of contact. Because slot 58 confines the movement of the retention post 50 to translation in the direction of the slot 58, the center 76 of the pinion 29 is allowed to move in one of two opposing directions. Thus, turning the pinion 29 extends or retracts the lens 22 to one of the previously discussed lens positions by moving the retention post 50 among the locations 64–68 in the slot 58. Although the rack 70 has four teeth 72, the rack 70 can have any number of teeth 72 sufficient to move the retention post 50 to all the locations 64–68 or more locations if applicable.

Referring back to FIG. 1, the goggle 20 also comprises a lens stabilizer 78 that helps retain the lens 22 in the various lens positions. In this and certain other embodiments, the lens stabilizer 78 comprises a top 80, and a bottom 82 substantially identical to the top 80, and can be made of any suitably resilient material. The stabilizer 78 can be attached to the frame 24 and lens 22 in any desired manner. For example, extending from the top and bottom 80 and 82 in opposite directions are stabilizer posts 84. Stabilizer slots 86 sized to receive and retain the stabilizer posts 84 adjustably retain the lens stabilizer 78 to the frame 24. The slots 86 can be located in the frame 24 so that retention of retention post 50 in one of the locations 64–68 (FIG. 3A) corresponds to the retention of the stabilizer posts 84 in corresponding locations in the slots 86. In some embodiments, the lens 22 can pivot among the positions. For example, the bottom 82 of the stabilizer 78 can move relative to the frame 24, and the lens 22 can pivot about the top 80. Or, the top 80 can move relative to the frame 24 and the lens 22 can pivot about the bottom 82. Or, neither the top 80 nor bottom 82 moves relative to the frame 24, and two sections of the lens 22—the one in front of the left eye and the one in front of the right eye when worn—can pivot about the stabilizer 78. The pivot angle—the angle formed between the lens 22 or a position of the lens 22 and frame 24 when the lens 22 is located in any of the positions—is defined such that the lens 22 remains in front of at least one eye of the user to provide substantial undiminished protection, e.g., the pivot angle typically ranges between 0 and 30 degrees inclusive but can include the ranges between 0 and 10 degrees or 0 and 20 degrees or any other desired range. The clips 88 can releasably attach the lens 22 to the lens stabilizer 78. Thus, when conditions require a different lens 22, a user can quickly and easily remove the unwanted lens and can install the desired lens. For example, such quick replacement can provide for changing lens tints or laser protections or other features as desired. Quick lens replacement can be achieved using other replacement mechanisms as desired. However, when quick and easy substitution of the lens 22 is not desired, the lens 22 can be securely attached to the lens stabilizer 78 and lens posts 48 by any desired method. In addition, the lens stabilizer 78 can help adjustment mechanism 28 retain the lens 22 to the frame 24, or the lens stabilizer 78 may retain the lens 22 to the frame 24 by itself.

Still referring to FIG. 1, the lens 22 can protect a user's eyes from bright or harmful light as well as particles suspended in the ambient air and other matter. The lens 22 is typically made of any desired light transmissive material. For example, if desired, the lens can be substantially clear and transmit substantially all light that contacts the lens. However, when specific conditions like bright light, very low light or high intensity collimated light, e.g., laser beams, or objects with high kinetic energy exist, lenses specifically designed for the condition may be used. For example, a tinted or polarized lens may be made from a light tinting or light polarizing material, or made by attaching a tinted or polarized film to the lens 22. Furthermore, the tinting material or film may filter a narrow range of light wavelengths such as those corresponding to the light wavelengths emitted by lasers or welding torches. Also, the material of the lens 22 can be impact resistant as well as shatter proof like ballistic grade lenses. The lens 22 may also selectively attenuate infrared light or light having a wavelength greater than approximately 670 nanometers. In addition, the lens 22 may attenuate ultraviolet light or light having a wavelength less than approximately 420 nanometers. Or, the lens 22 may attenuate both infrared and ultraviolet light. In addition, the lens 22 can include "tear aways"—removable sheets covering the outside surface of the lens. By simply pulling off a "tear away", a muddied or oiled lens can be quickly and easily cleaned.

Still referring to FIG. 1, the frame 24 further comprises frame vents 90 covered with filter elements 92. The frame vents 90 and filter elements 92 can be located to provide filtered ventilation, which is one form of inhibited airflow, of the enclosed environment when the lens 22 is in the first position or the second position as desired. 20 Thus, if desired, in dusty or snowy environments some degree of ventilation can be maintained without exposing one's eyes to the dust or snow. And, if desired, in humid ambient environments or during strenuous physical activities, a user can move the lens to a position that permits inhibited and/or uninhibited air flow to help remove or reduce the possibility of condensation forming on the inside surface of the lens 22. In some embodiments of the goggle 20, the frame 24 may comprise frame vents that are not covered with filter elements. In other embodiments of the goggle 20 the frame need not include frame vents. For this and other reasons, the profile—the distance from the user's eyes to the lens 22—of the goggle 20 when the lens 22 is in the first position can be reduced. In some conditions, such as windy conditions like those found on aircraft carrier decks or while skydiving, the goggle 20 may be more likely to remain in front of the user's eyes than goggles having a larger frame size.

Still referring to FIG. 1, the goggle-retention member 34 typically has a first end connected to a left side 36 of the frame and a second end connected to a right side 38 of frame 24 and typically has a length sufficient to wrap around a user's head to removably secure the goggle 20 to the user's face. The goggle-retention member 34 can be releasably or fixedly connected to the sides 36 and 38, or goggle-retention member 34 can be slidingly connected to the sides 36 and 38 as shown in FIG. 1. Furthermore, goggle-retention member 34 can be made of two or more straps that buckle together or can be a single adjustable elastic strap as shown in FIG. 1. Also, left and right temple pieces can be pivotally connected to the sides 36 and 38 and may be used to retain the frame 24 to a user's face.

Although the goggle 20 discussed above uses the lens-retention/adjustment mechanism 28, other lens-retention and adjustment mechanisms discussed elsewhere herein or containing other adjustment or retention mechanisms as desired may be incorporated by the goggle 20. In addition, for example, the lens portion 42 and the frame portion 44 can be attached to or formed in the lens 22 and frame 24 (or other suitable structure) other than as shown and discussed herein.

Figure 5A:
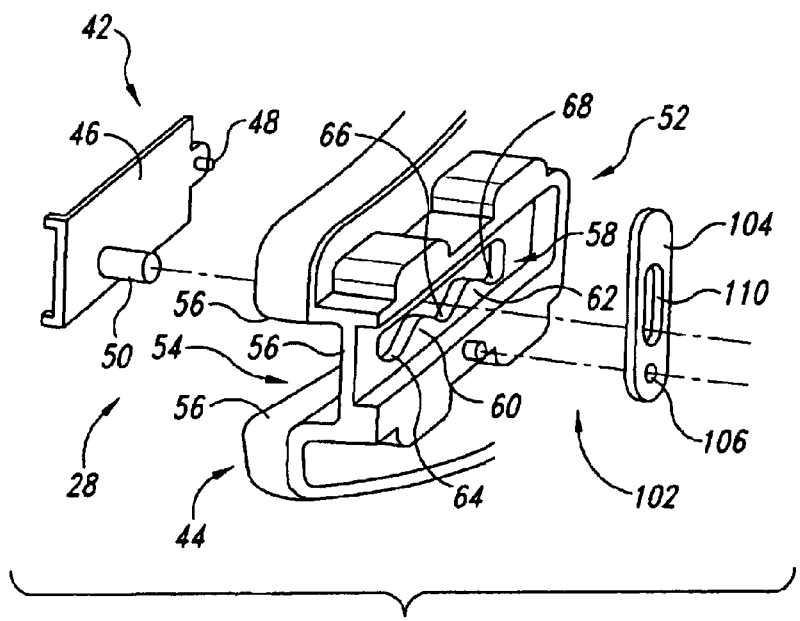
FIG. 5A is an exploded perspective view of the lens-retention and adjustment mechanism shown in FIG. 4.
Figure 5B:
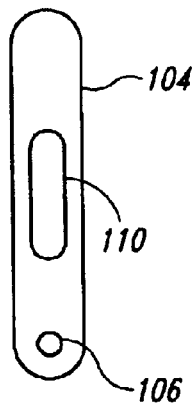
FIG. 5B is a plan view of the lever shown in FIGS. 4 and 5A.

FIGS. 4–5B are views of a pivoted goggle 100 according to another embodiment of the invention. FIG. 4 is a perspective view of the pivoted goggle 100 and illustrates lens 22 retained in a given position relative to frame 24. FIG. 5A is an exploded view of the levered adjustment mechanism 102 of FIG. 4, which mechanism also retains lens 22 to frame 24. FIG. 5B is a plan view of the lever 104 used to pivot the lens 22 to the lens positions previously discussed. By turning the lever 104, a user can pivot the lens 22 between the various positions while maintaining the lens 22 in front of at least one eye of the user to provide substantial, undiminished protection. More specifically, a portion of the lens periphery 30 of the lens 22 remains in contact with a portion of the lens contacting surface 32 of the frame 24 when the lens 22 is in the second or third positions, and the pivot angle, discussed elsewhere herein, formed between the lens 22 and frame 24 typically ranges between 0 and 30 degrees inclusive.

Referring to FIGS. 5A and 5B, as depicted levered adjustment mechanism 102 comprises lever 104 that includes a pivot hole 106 where it is rotatably attached to the frame portion 44, and a slide channel 110, where it is slidingly attached to the retention post 50. Both attachments can be made using methods such as pins, bolts and washers, bearings, interference fit between the corresponding parts, for example an enlarged portion of the retention post 50 relative to the pivot hole 106, or otherwise as desired. The slide channel 110 is appropriately sized to accommodate the slight movement of the retention post 50 along the lever 104 as the lever 104 is rotated about its pivot hole 106. In other embodiments, the lever 104 may be rotatably attached to the lens portion 42 and may be slidingly attached to the frame portion 44. In addition, although the lever 104 is shown attached substantially parallel to the frame portion 44, the lever 104 may be attached at any desired angle to the frame portion 44 or substantially perpendicular to the frame portion 44, or otherwise as desired provided that movement of the lever imparts movement of the lens 22 relative to the frame 24.

Referring back to FIG. 4, pivot lens stabilizer 118 retains the lens 22 in the various lens positions. In this and certain other embodiments, the pivot lens stabilizer 118 comprises a top 80 and a bottom 82, can be made of any resilient material, and can be attached to the frame 24 or lens 22 in any desired manner. For example, a stabilizer to post 84 can extend from the top 80 into a stabilizer slot 86 sized to receive and adjustably retain the stabilizer post 84 while the bottom 82 can be pivotally attached to the frame 24. The slot 86 can be located in the frame 24 so that the retention of the retention post 50 in one of the locations 64–68 (FIG. 5A) corresponds to the retention of the post 84 in corresponding locations in the slot 86. In another example, the pivot lens stabilizer 118 may not move relative to the frame 24 as two sections of the lens 22—the one in front of the left eye and the one in front of the right eye when worn—pivot about the stabilizer 78 among the lens positions. The clips 88 can releasably attach the lens 22 to the pivot lens stabilizer 118. Thus, when conditions require a different lens 22, one can quickly and easily remove the unwanted lens and install the desired lens. However, when quick and easy substitution of the lens 22 is not desired, the lens 22 can be attached securely to the pivot lens stabilizer 118 and lens posts 48. The lens stabilizer 118 can help a separate lens-retention mechanism 28 retain the lens 22 to the frame 24, or the pivot lens stabilizer 118 may retain the lens 22 to the frame 24 by itself.

Although the pivoted goggle 100 discussed above uses levered adjustment mechanism 102, other lens-retention and adjustment mechanisms discussed elsewhere herein or containing other adjustment or retention mechanisms as desired may be incorporated within pivoted goggle 100. For example, the lever can be pivotally attached at one end to the frame and then directly attached to the lens such that pushing or pulling the lever (for example at a tab or button extending beyond the lens attachment point) extends and retracts the lens relative to the frame. The lens portion 42 and the frame portion 44 can be attached to or formed in either the lens 22 or frame 24 (or other suitable structure) in any desired fashion.

Figure 6:
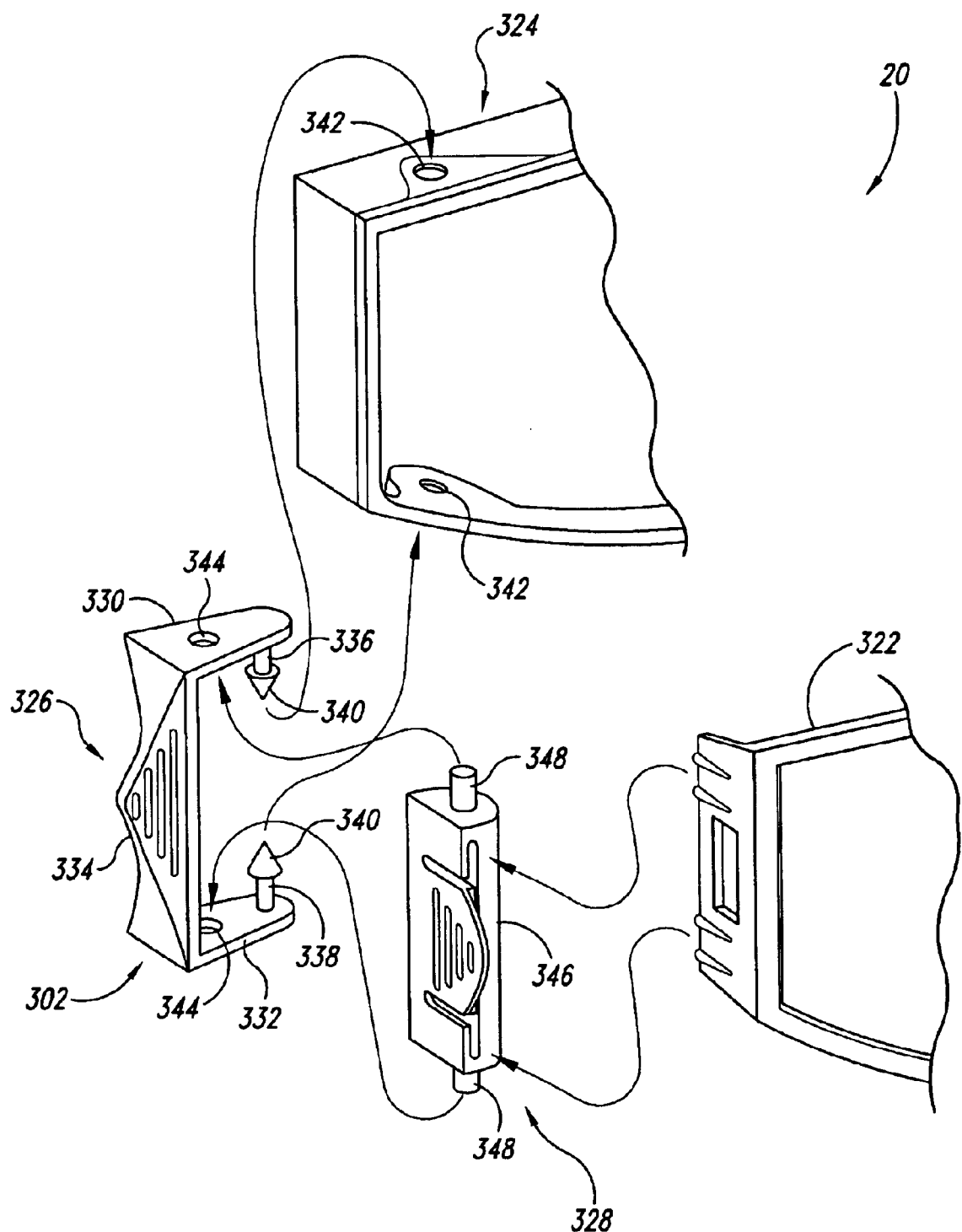
FIG. 6 is a partial perspective view of a goggle according to another embodiment of the invention.

FIG. 6 is an exploded perspective view of another levered adjustment mechanism 302 incorporated in an goggle 20 according to an embodiment of the invention. As depicted, the levered adjustment mechanism 302 combines a retention mechanism and adjustment mechanism to releasably retain a removable lens 322 to the frame 324 and move the removable lens 322 among the various lens positions discussed elsewhere herein. Similar to other adjustment mechanisms discussed herein, the levered adjustment mechanism 302 moves the removable lens 322 among the different lens positions by moving the whole removable lens 322 substantially the same distance away from the frame 324 and does not pivot the removable lens 322 among the different lens positions.

In this and certain other embodiments, the levered adjustment mechanism 302 shown in FIG. 6 comprises a swing-arm 326 rotatably attachable to the frame 324 and a swing-arm axle 328 rotatably attachable to the swing-arm 326 and releasably attachable to the removable lens 322. In some embodiments, the swing-arm 326 includes an upper tab 330 and a lower tab 332 extending from opposite ends of a thumb tab 334. An upper swing-arm post 336 extends from the upper tab 330 and typically toward the lower tab 332, and a lower swing-arm post 338 extends from the lower tab 332 and typically toward the upper tab 330. Each swing-arm post 336 and 338 includes an end 340 forcibly insertable into a frame-attachment hole 342 yet configured and composed of any desired resilient material such as rubber or plastic to prevent easy removal of swing-arm post 336 or 338 from the frame 324. In other embodiments, the swing-arm posts 336 and 338 can extend in any direction that permits their insertion into the frame attachment holes 342 and the swing-arm post ends 340 can be rotatably attachable to the frame attachment holes 342 using desired fastening techniques such as screws or bolts with washers or bushings. Once inserted, the swing-arm 326 is rotatable about the frame attachment holes 342 by pushing or pulling the thumb tab 334 as desired. The upper and lower tabs 330 and 332 also include an axle hole 344 typically located between the thumb tab 334 and the upper and lower swing-arm posts 336 and 338 respectively, to receive and retain the swing-arm axle 328. In other embodiments, the axle holes 344 can be located anywhere on the swing-arm 326 relative to the swing-arm posts 336 and 338 that permits movement of the axle holes 344 as the swing-arm 326 rotates relative to the frame 324.

Still referring to FIG. 6, the swing-arm 326 can be made of any desired material such as rubber, plastic, metal or any combination of these materials. The upper and lower tabs 330 and 332 can be integrally formed with the thumb tab 334 or attached to the thumb tab 334 using desired fastening techniques such as adhesive bonding or mechanical fasteners such as screws or rivets. The swing-arm posts 336 and 338 can be integrally formed with their respective tabs 330 and 332 or attached to their respective tabs 330 and 332 using desired fastening techniques such as adhesive bonding or mechanical fasteners such as screws or rivets.

Still referring to FIG. 6, in some embodiments of the levered adjustment mechanism 302, the swing-arm axle 328 comprises an axle body 346 releasably attachable to the removable lens 322 and two axle posts 348 insertable into the axle holes 344. The axle posts 348 typically extend from the axle body 346 in opposite directions and are sufficiently sized to extend into their respective axle hole 344 to rotatably attach the swing-arm axle 346 to the swing-arm 326. In other embodiments, desired fastening techniques such as screws or bolts with washers or bushings can be used to rotabably attach the swing-arm axle 346 to the swing-arm 326. The swing-arm axle 346 can be made of any desired material such as rubber, plastic, metal or a combination of these materials and the axle posts 348 can be integrally formed with the axle body 346 or attached to the axle body 346 using desired fastening techniques such as adhesive bonding or mechanical fasteners such as screws or rivets. The axle body 346 is releasably attached to the removable lens 322 to allow a user to quickly and easily remove the removable lens 322 from the axle body 346, and thus, the frame 324 when a new or different lens is desired. For example a different lens may be desired when the light conditions change from overcast or soft sun light to clear skies or bright sun light.

Still referring to FIG. 6, to move the removable lens 322 among the positions, a user simply rotates the swing-arm 326 by pushing or pulling the thumb tab 334. As the swing-arm 326 rotates relative to the frame 324, the swing-arm axle 328 moves away from or toward the frame 324 and rotates relative to the swing-arm 326 in an opposite direction. This opposite rotation of the swing-arm axle 328 cancels out the rotation of the swing-arm 326, and thus, the removable lens 322 substantially moves away from or toward the frame 324 without rotating or pivoting relative to the frame 324.

Although the levered adjustment mechanism 302 depicted in FIG. 6 combines an adjustment mechanism and retention mechanism into one adjustment mechanism, the levered adjustment mechanism 302 can be combined with other retention mechanisms discussed herein or as otherwise desired. Furthermore, although the swing-arm 326 is discussed and shown with two swing-arm posts 336 and 338, one, three or other quantities can be used, and although the swing-arm axle 328 is discussed and shown with two axle posts 348, one, three or other quantities can be used. In addition, although the swing arm 326 includes swing-arm posts 336 and 338, and the swing-arm axle 328 includes axle holes 344 as discussed and shown, the swing arm 326 can include the axle holes 344 and the swing-arm axle 328 can include the swing-arm posts 336 and 338.

Figure 7:
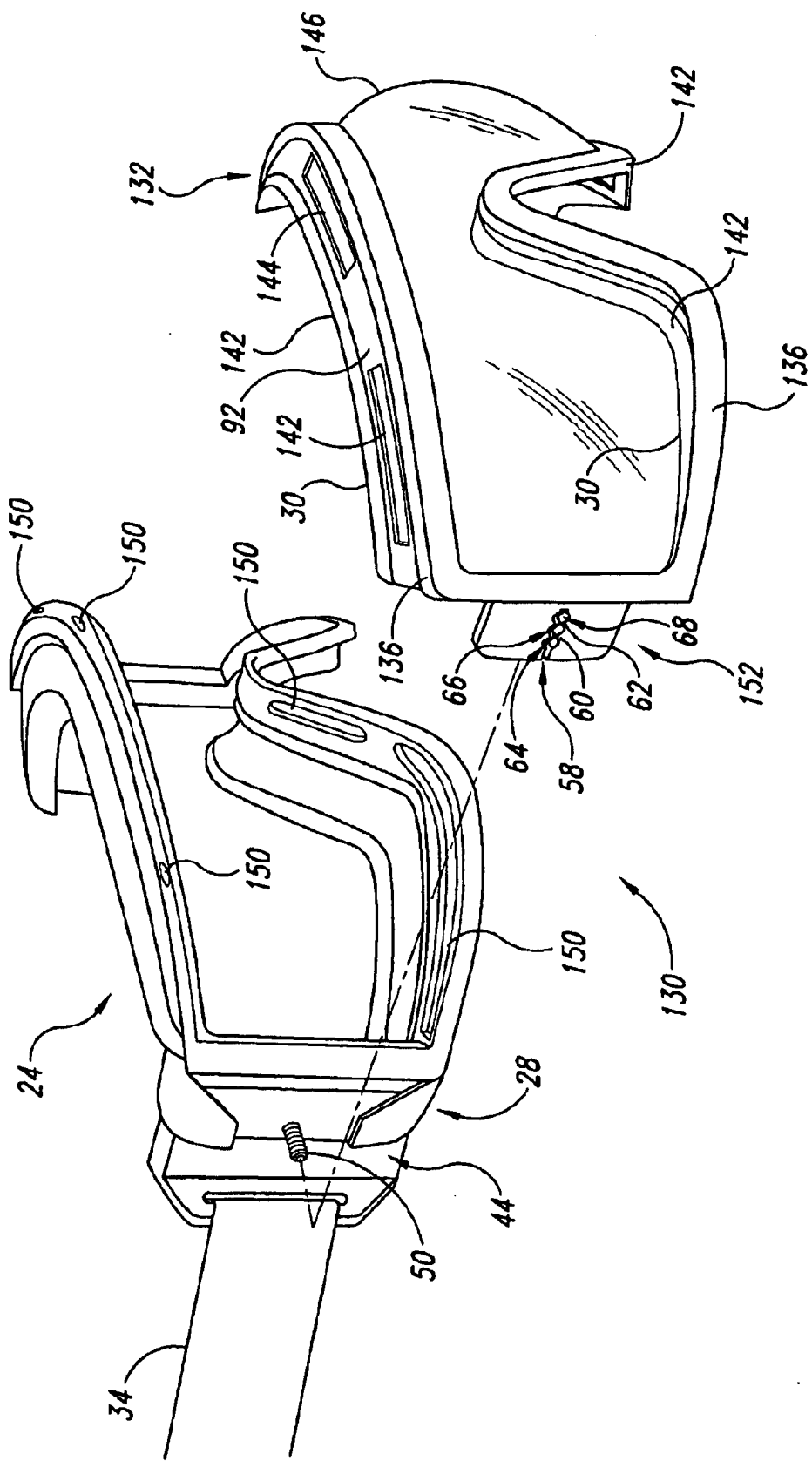
FIG. 7 is an exploded perspective view of a goggle according to another embodiment of the invention.
Figure 8A:
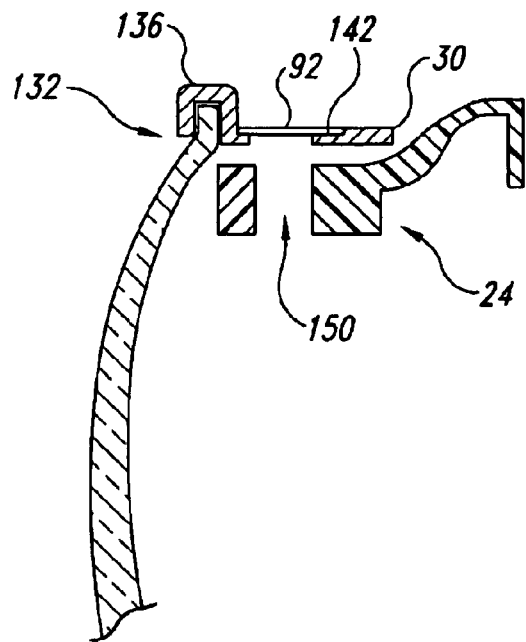
FIG. 8A is a partial cross-sectional view of the goggle of FIG. 7 assembled, illustrating the lens retracted to the frame to decrease ventilation of the goggle.
Figure 8B:
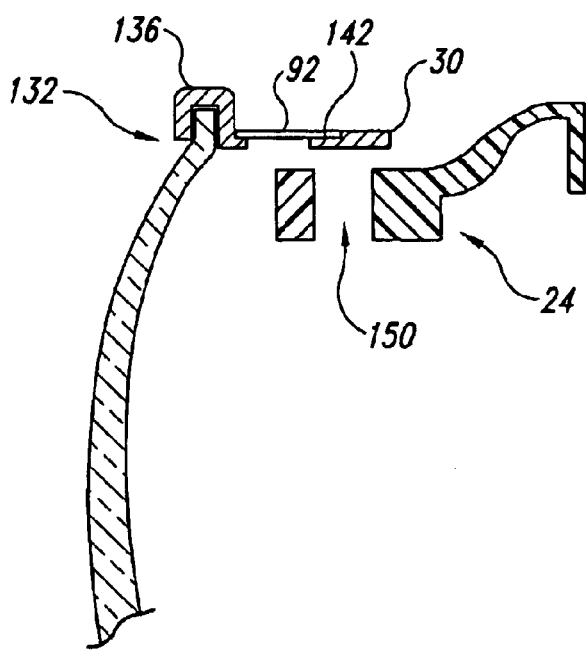
FIG. 8B is a partial cross-sectional view of the goggle of FIG. 7 assembled, illustrating the lens extended away from the frame to increase ventilation of the goggle.

FIGS. 7–8B are views of a double-framed goggle 130 according to another embodiment of the invention. FIG. 7 is an exploded view of the double-framed goggle 130. FIG. 8A is a partial cross section of the lens assembly 132 and frame 24 of the double-framed goggle 130 in FIG. 7 assembled, and illustrates the lens assembly 132 in a first position. FIG. 8B is a similar partial cross section to that shown in FIG. 8A illustrating the lens assembly 132 in a third position. The lens assembly 132 includes a lens periphery 30 that comprises a lens frame 136. Lens frame 136 can comprise elements added to frame, such as an extra plastic frame as depicted, as well as components of the lens itself shaped, molded, formed or otherwise produced, to function as a frame and, typically, not a part of the lens. The lens assembly 132 is moved among the various lens positions by simply pushing or pulling the lens assembly 132. The adjustment and lens-retention mechanism are combined into one adjustment mechanism 28.

FIG. 7 depicts a curved lens 146. In the embodiment depicted in FIG. 7, the adjustment mechanism 28 comprises a lens frame portion 152 comprising a portion of the lens periphery 30, and a frame portion 44. The lens frame portion 152 comprises a slot 58 and first and second detents 60 and 62, and the frame portion 44 comprises a retention post 50. The slot 58 is sized to receive the retention post 50. Appropriately sized and spaced along the slot 58, the detents 60 and 62 define three locations 64, 66 and 68 where the detents 60 and 62 confine the retention post 50 of the lens frame portion 152 from freely moving among the locations 64–68. These locations 64–68 respectively correspond to the first, second and third positions of the lens assembly 132. In some embodiments, the lens frame portion 152 may include a bar or other handle-type device protruding from the lens frame portion 152 to help the user grasp and move the lens assembly 132 among the lens positions. Although three locations are shown and discussed corresponding to three lens positions, more or less locations corresponding to more lens positions are possible. Consequently, the slot 58 can have any number of detents to correspond with the number of lens positions.

In the embodiment depicted in FIGS. 8A and 8B, as well as certain other embodiments, the frame 24 and the lens frame 136, or other desired structures that move relative to each other upon movement of the lens assembly 132 relative to the frame 24, can comprise one or more corresponding frame vents 150 or lens vents 142, respectively, that can have filter elements 92 covering either or both vents 150 and 142. The level of air flow through the vents 150 and 142 can be varied according to the position of the lens assembly 132 relative to the frame 24. For example, in one position, such as shown in FIG. 8A, the vents 142 and 150 substantially align to form a passage such that air passes through the aligned vents 142 and 150. In another position, such as shown in FIG. 8B, the vents 150 and 142 can be non-aligned, such that any air that passes through a given lens vent 142 or frame vent 150 does not have any substantial corresponding effect from its corresponding frame vent 150 or lens vent 142. As also shown in FIGS. 8A and 8B, the frame 24 and lens frame 136 can be placed in different positions such that air can pass between the frame and lens, or be blocked from such passage, in addition to the alignment, partial alignment or non-alignment of the vents 150 and 142.

If desired, the vents 142 and 150 can substantially align in two or more positions, for example one position that provides either a totally blocked or a totally filtered passageway, another position that provides a partially blocked or partially filtered passageway, and still another position that provides an uninhibited, or non-filtered, passageway. In addition, if desired, the material surrounding a vent 142 or 150 can be designed to block a corresponding vent 150 or 142 in one position but not another; in such embodiments, the air can be substantially or completely prevented from passing through a given vent 142 or 150.

Although the double-framed goggle 130 discussed above uses the adjustment mechanism 28, other lens-retention and adjustment mechanisms discussed elsewhere herein or containing other adjustment or retention mechanisms as desired may be incorporated within double-framed goggle 130. In addition and as desired, the lens frame portion 152 and the frame portion 44 can be attached to or formed in the lens assembly 132 and frame 24 (or other suitable structure) other than as shown or discussed herein.

Figure 9:
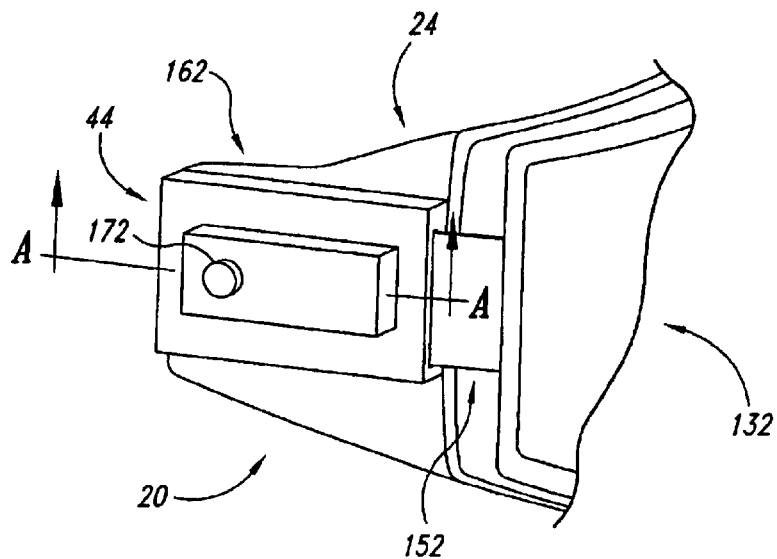
FIG. 9 is a partial perspective view of a goggle according to another embodiment of the invention.
Figure 10:
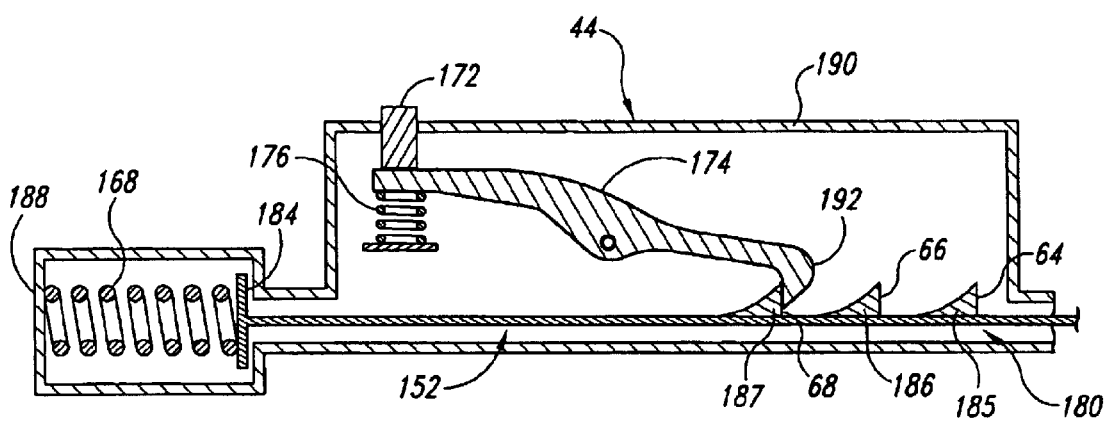
FIG. 10 is a cross-sectional view along line a—a of the lens-retention and adjustment mechanisms shown in FIG. 9

FIGS. 9 and 10 are views of a hook and pawl adjustment mechanism 162 incorporated in an goggle 20 according to another embodiment of the invention. FIG. 9 is a perspective view of hook and pawl adjustment mechanism 162 and illustrates the lens assembly 132 in the third position. FIG. 10 is a cross section of hook and pawl adjustment mechanism 162 respectively of FIG. 9 taken at line A—A. The adjustment mechanism 162 includes a spring 168 that biases the lens assembly 132 to a second or third position, or other position as desired, and the hook and pawl adjustment mechanism 162 retains the lens assembly 132 in desired lens positions.

FIGS. 9 and 10 depict a hook and pawl adjustment mechanism 162 comprising a frame portion 44 comprising a button 172 and pawl 174 that is biased in a restraining position by a pawl bias spring 176, and a lens frame portion 152 comprising a toothed rack 180. To move the lens assembly 132 away from the first position, the user can push the button 172, which disengages the pawl 174 from the toothed rack 180 and allows the lens bias spring 168 to move the lens assembly 132 away from the frame 24. To move the lens assembly 132 toward the first position, the user applies force, for example by pushing or pulling with his or her hand, against the lens assembly 132 toward the frame 24. As the lens assembly 132 moves toward the frame 24, the toothed rack 180 slides under the pawl 174 biased in a retaining position. Once the desired position is obtained, the user can stop pushing and can allow the pawl 174 to prevent movement of the lens assembly 132 away from the first position.

Referring to FIG. 10, the lens frame portion 152 further comprises a lens frame end 184, and the toothed rack 180 comprises first, second and third teeth 185, 186 and 187. The frame portion 44 further comprises a frame end 188 and a housing 190, and the pawl 174 comprises a hook 192. To bias the lens assembly 132 in the third position, the lens bias spring 168 can be compressed between the lens frame end 184 and the frame end 188. Appropriately sized, the spring 168 typically applies sufficient force to maintain the lens assembly 132 in the third position, for example in windy conditions, yet provide for quick and easy retraction of the lens 22. The pawl 174 can be rotatably attached to the housing 190 and can be biased by the pawl bias spring 176 such that the hook 192 remains in contact with the teeth 185–187 when the button 172 is not pressed the restraining position. The teeth 185–187 and hook 192 can be shaped to permit movement of the lens assembly 132 toward the frame 24 by allowing the teeth 185–187 to slide under the hook 192, and prevent movement of the lens assembly 132 away from the frame 24 when the button 172 is not pressed. Appropriately sized and spaced along the lens frame portion 152, the teeth 185, 186 and 187 also define three locations 64, 66 and 68 respectively corresponding to the previously discussed lens positions. Although three locations are shown and discussed 20 corresponding to three lens positions, more or less locations corresponding to more lens positions are possible. Consequently, the toothed rack 180 can have any number of teeth and can have any number of lens positions.

Although the goggle has been described in considerable detail with reference to certain embodiments for purposes of illustration, other embodiments are possible. Therefore the spirit and scope of the appended claims should not be limited to the above description of the embodiments; the present inventions include suitable modifications as well as all permutations and combinations of the subject matter set forth herein.

What is claimed is:

1. A goggle comprising:

a single-piece lens having a lens periphery;

a frame having a lens contacting surface, the frame sized to maintain the single-piece lens in front of at least one eye of a user;

a lens-retention mechanism between the single-piece lens and the frame that retains the single-piece lens and the frame in a first position that maintains the single-piece lens in front of the at least one eye of the user and permits a first level of air flow between the single-piece lens and the frame, and in a second position that maintains the single-piece lens in front of the at least one eye of the user and permits a second, substantially greater level of air flow between the single-piece lens and the frame; and an adjustment mechanism between the single-piece lens and the frame that moves the single-piece lens relative to the frame among the positions.

2. The goggle of claim 1 wherein the goggle comprises two adjustment mechanisms, one adjustment mechanism on either side of the lens and frame.

3. The goggle of claim 1 wherein the first level of air flow is substantially zero.

4. The goggle of claim 1 wherein the second position is defined such that substantially all of the lens periphery is located varying distances away from the lens contacting surface.

5. The goggle of claim 1 wherein the second position is defined such that substantially all of the lens periphery is located a first, substantially constant distance away from the lens contacting surface.

6. The goggle of claim 1 wherein the lens pivots among the positions.

7. The goggle of claim 1 wherein the second position is defined such that a portion of the lens periphery contacts the lens contacting surface.

8. The goggle of claim 1 wherein the lens-retention mechanism further retains the lens in a third position that maintains the lens in front of the at least one eye of the user and permits a third level of air flow between the lens and the frame that is substantially greater than the second level of air flow.

9. The goggle of claim 1 wherein the lens is removably attached to the frame.

10. The goggle of claim 1 wherein the lens is selected from at least one of the group consisting of a polarized lens, a tinted lens or a ballistic grade lens.

11. The goggle of claim 1 wherein the lens selectively attenuates wavelengths of light from at least one of the group consisting of infrared light, ultraviolet light, or a narrow range of light wavelengths corresponding to light wavelengths emitted by a laser or a welding torch.

12. The goggle of claim 1 wherein the frame comprises a face-contoured perimeter that forms a substantially air-tight seal with a user's face when the the goggle is worn by a user.

13. The goggle of claim 12 further comprising a goggle-retention member comprising an elastic strap having a length, a first end connected to a left side of the frame and a second end connected to a right side of the frame.

14. The goggle of claim 13 wherein the length is adjustable.

15. The goggle of claim 1 wherein the frame comprises one or more frame vents.

16. The goggle of claim 15 wherein the vents are covered with a filter element.

17. The goggle of claim 1 wherein the lens-retention mechanism comprises a post and at least first and second detents sized to receive the post and located such that when the lens is in the first position the first detent retains the post.

18. The goggle of claim 17 wherein the adjustment mechanism comprises at least one of the group consisting of a rack and pinion or a lever, the adjustment mechanism operably connected to the lens and frame to move the lens among the first and the second positions.

19. The goggle of claim 1 wherein the adjustment mechanism comprises at least one of the group consisting of a rack and pinion, a lever or a swing arm, the adjustment mechanism operably connected to the lens and frame to move the lens among the first and the second positions.

* * * * *